US008802053B2

(12) United States Patent
Kim et al.

(10) Patent No.: US 8,802,053 B2
(45) Date of Patent: *Aug. 12, 2014

(54) RADIO-METHYL VOROZOLE AND METHODS FOR MAKING AND USING THE SAME

(71) Applicant: Brookhaven Science Associates, LLC, Upton, NY (US)

(72) Inventors: Sung Won Kim, Port Jefferson, NY (US); Anat Biegon, Port Jefferson, NY (US); Joanna S. Fowler, Bellport, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/847,136

(22) Filed: Mar. 19, 2013

(65) Prior Publication Data
US 2013/0225831 A1 Aug. 29, 2013

Related U.S. Application Data

(62) Division of application No. 12/704,114, filed on Feb. 11, 2010.

(60) Provisional application No. 61/152,356, filed on Feb. 13, 2009.

(51) Int. Cl.
*A61K 51/00* (2006.01)
*A61M 36/14* (2006.01)

(52) U.S. Cl.
USPC .......................................... 424/1.81; 548/257

(58) Field of Classification Search
None
See application file for complete search history.

(56) References Cited

U.S. PATENT DOCUMENTS 4,943,574 A 7/1990 Raeymaekers et al.
5,663,354 A 9/1997 Willemsens et al.

OTHER PUBLICATIONS

Erlandsson et al. J Label. Compd. Radiopharm. 2008, 51, 207-212.*
Rasmussena et al. Sep. Sci. Tech. 2007, 8, 353-371.*
Csato et al. J. Chrom. 1990, 511, 79-88.*
Euerby et al. J. Chrom. A 2007, 1154, 138-151.*
Przybyciel et al. LCGC Column Tech. Supp. 2004, 26-29.*
Lindstrom et al. Nucl. Med. Biol. 1998, 25, 497-501.*
Abdelgadir, S., et al., "Distribution of Aromatase Cytochrome P450 Messenger Ribonucleic Acid in Adult Rhesus Monkey Brains," *Biology of Reproduction*, vol. 57, pp. 772-777, 1997.
Biegon, A., et al., "Unique Distribution of Aromatase in the Human Brain: In Vivo Studies with PET and [N-methyl-$^{11}$C] Vorozole," *Synapse*, vol. 64, pp. 801-807, 2010.
Brunetti, J., "Current Status of Positron Imaging for Breast Cancer," [online], [retrieved Jan. 14, 2009], <URL:http://www.cancernews.com/data/Article/260.asp>(4 pages).
Carta, A., et al., "1H, 6H-triazolo [4,5-e] benzotriazole-3 Oxides and 5,5-(Z)-diazene-1,2-diylbis (2-methyl-2H-1,2,3-benzotriazole) Derived from Chloronitrobenzotriazoles and Hydrazine," *Heterocycles*, vol. 65, pp. 2471-2481, 2005.
De Coster, R., et al., "New Non-steroidal Aromatase Inhibitors: Focus on R76713," *The Journal of Steroid Biochemistry and Molecular Biology*, vol. 37, pp. 335-341, 1990.
De Coster, R., et al., "Antitumoral and Endocrine Effects of (+) Vorozole in Rats Bearing Dimethylbenzanthracene-induced Mammary Tumors," *Cancer Research*, vol. 52, pp. 1240-1244, 1992.
De Knaep, A., et al., "Development Summary Towards a Manufacturable Process for R 83842[(S)-6-[(4-chlorophenyl) (1H-1,2,4-triazol-l-yl)methyl]-1-methyl-1H-benzotriazole]," *Organic Process Research& Development*, vol. 4, pp. 162-166, 2000.
Ding Y., et al., "Comparative Evaluation of Positron Emission Tomography Radiotracers for Imaging the Norepinephrine Transporter: (S,S) and R, R) Enantiomers of Reboxetine Analogs (I$^{11}$C] methylreboxetine, 3-Cl-[$^{11}$C] methylreboxetine and [$^{18}$F] fluororeboxetine), (R) -[$^{11}$C] nisoxetine, [$^{11}$C] oxaprotiline and [$^{11}$C] lortalamine," *Journal of Neurochemistry*, vol. 94, pp. 337-351, 2005.
Kil, K., et al., "Synthesis and PET Studies of [$^{11}$C] letrozole, an Aromatase Inhibitor Drug," *Journal of Nuclear Medicine*, vol.49 (Supplement 1):285P [online], [retrieved Apr. 5, 2012], <URL:http://jnumedmtg.snmjournals.org/cgi/content/meeting . . . abstract/49/MeetingAbstracts ... 1/285P-c>(2 pages).
Kil, K., et al., "Synthesis and PET Studies of [$^{11}$C-cyano] letrozole (Femara), an Aromatase Inhibitor Drug," *Nuclear Medicine and Biology*, vol. 36, pp. 215-223, 2009.
Kim, S., et al., "Reinvestigation of the Synthesis and Evaluation of [N-methyl-11C] Vorozole, a Radiotracer Targeting Cytochrome P450 Aromatase," Nuclear Medicine and Biology, vol. 36, pp. 323-324, 2009.
Kopanska, K., et al., "Synthesis and Activity of 1*H*-benzimidazole and 1*H*-Benzotriazole Derivatives as Inhibitors of *Acanthamoeba castellan*." *Bioorganic and Medicinal Chemistry*, vol. 12, pp. 2617-2624, 2004, and Corrigendum (1 page).
Lindström, P., et al., "Synthesis, In Vivo Rhesus Monkey Biodistribution and In Vitro Evaluation of a $^{11}$C-Labelled Potent Aromatase Inhibitor: [*N-methyl-*$^{11}$ C] Vorozole," *Nuclear Medicine & Biology*, vol. 25 pp. 497-501, 1998.
Miki, Y., et al., "Controversies of Aromatase Localization in Human Breast Cancer—Stromal versus Parenchymal Cells," *The Journal of Steroid Biochemistry and Molecular Biology*, vol. 106, pp. 97-101, 2007.

(Continued)

*Primary Examiner* — Michael G Hartley
*Assistant Examiner* — Sean R Donohue
(74) *Attorney, Agent, or Firm* — Dorene M. Price; Christine L. Brakel

(57) ABSTRACT

Radiotracer vorozole compounds for in vivo and in vitro assaying, studying and imaging cytochrome P450 aromatase enzymes in humans, animals, and tissues and methods for making and using the same are provided. [N-radio-methyl] vorozole substantially separated from an N-3 radio-methyl isomer of vorozole is provided. Separation is accomplished through use of chromatography resins providing multiple mechanisms of selectivity.

21 Claims, 3 Drawing Sheets

(56) References Cited

OTHER PUBLICATIONS

Reichel, A., et al., "Potential of Immobilized Artificial Membranes for Predicting Drug Penetration Across the Blood-Brain Barrier," *Pharmaceutical Research*, vol. 15, pp. 1270-1274, 1998.

Seralini, G., et al., "Aromatase Inhibitors: Past, Present and Future," *Molecular and Cellular Endocrinology*, vol. 178, pp. 117-131, 2001.

Takahashi, K., et al., "Imaging of Aromatase Distribution in Rat and Rhesus Monkey Brains with [$^{11}$C] vorozole3," *Nuclear Medicine and Biology*, vol. 33, pp. 599-605, 2006.

Venet, M., et al., "Vorozole, Selective Inhibitor of Aromatase," *Actualités de Chimie Thérapeutique*, vol. 23, pp. 239-246, 1997.

Wouters, W., et al., "Aromatase Inhibition by R 76713: Experimental and Clinical Pharmacology," *Journal of Steroid Biochemistry*, vol. 34, pp. 427-430, 1989.

Wouters, W., et al., "R 76713, A New Specific Non-steriodal Aromatase Inhibitor," *Journal of Steroid Biochemistry*, vol. 32, pp. 781-788, 1989.

Wouters, W., et al., "Comparative Effects of the Aromatase Inhibitor R76713 and of its Enantiomers R83839 and R86842 on Steriod Biosynthesis In Vitro and In Vivo," *Journal of Steroid Biochemistry*, vol. 37, pp. 1049-1054, 1990.

Ozawa, M., et al., "PET of Aromatase in Gastric Parietal Cells Using 11C-Vorozole," The Journal of Nuclear Medicine, vol. 52, No. 12, pp. 1964 to 1969, 2011.

Takahashi, K., et al., "Practical Synthesis of Precursor of [N-methyl-11c] Vorozole, an Efficient PET Tracer Targeting Aromatase in the Brain," Bioorganic & Medicinal Chemistry, vol. 19, pp. 1464 to 1470, 2011.

\* cited by examiner

RADIO-METHYL VOROZOLE AND METHODS FOR MAKING AND USING THE SAME

This application is a divisional of U.S. patent application Ser. No. 12/704,114, filed Feb. 11, 2010, which claims priority from U.S. Provisional Application 61/152,356 filed on Feb. 13, 2009, both of which are incorporated herein by reference in their entirety.

This invention was made with Government support under contract number DE-AC02-98CH10886, awarded by the U.S. Department of Energy and sponsored by the National Institutes of Health under grant number K05 DA 020001. The Government has certain rights in the invention.

FIELD OF INVENTION

Specific radiotracer vorozole compounds for in vivo and in vitro assaying, studying and imaging cytochrome P450 aromatase enzymes in humans, animals, and tissues and methods for making and using the same are provided.

BACKGROUND OF THE INVENTION

Cytochrome P450 aromatase, is the last enzyme in estrogen biosynthesis, catalyzing the conversion of androgens to estrogen. It plays a major role in the sexual differentiation of the brain during development and has been implicated in the brain response to injury and in the pathophysiology of Alzheimer's disease. The enzyme is highly expressed in liver, steroidogenic organs and specific regions of the brain including the amygdala, in the bed nucleus of the stria terminalis, the preoptic area (POA) and anterior hypothalamus. Moderate or lower levels have been observed in many other brain regions including posterior and lateral hypothalamic nuclei, hippocampus and temporal cortex of rodents, non-human primates and humans.

Aromatase activity can be inhibited reversibly or irreversibly by steroidal as well as non-steroidal compounds. Non-steroidal and steroidal aromatase inhibitors are used as adjuvant therapies for post-menopausal women having estrogen-dependent breast cancer. Examples of non-steroidal aromatase inhibitors approved for such use include letrozole (Femara®) and anastrozole (Arimidex®). These drugs have been shown to reduce the rate of recurrence of cancer in treated patients.

Aromatase inhibitor drugs are also used by body builders and athletes who abuse anabolic steroids, as a means of limiting the estrogenic side effects of excess androgens.

Radiotracer compounds that interact with the physiological targets of these drugs are useful for developing new forms of aromatase inhibitors as well as for monitoring the treatment efficacy of the drugs and for adjusting dosages.

Radiotracer compounds that specifically interact with P450 aromatase enzymes are further useful for studies on the location of the enzyme in tissue samples, for studying the enzyme mechanism of action and for kinetic studies on the synthesis and turnover of the enzyme in tissues.

Previous attempts to make use of [N-methyl-$^{11}$C]vorozole as a reliable, highly specific imaging tracer in positron emission tomography (PET) studies have been inexplicably unsuccessful, with the radiotracer exhibiting low regional specificity and high non-specific binding (see Lidström, et al. (1998) Nucl. Med. Biol. 25:497-501; Takahashi, et al. (2006) Neuroreport 19:431-435).

In addition, an attempt to make use of [$^{11}$C]letrozole as a specific radiotracer for studying brain aromatase enzymes in vivo (Kil, et al. (2008) J. Nucl. Med. 49 (Sup. 1):285P) found that the tracer was rapidly taken up in the brain and was then rapidly cleared. Pretreatment with unlabeled letrozole failed to block uptake. The rapid clearance of the [$^{11}$C]letrozole and lack of specific binding indicated that it was not a useful radiotracer for brain aromatase activity.

Thus, previous attempts to use radiotracer-labeled aromatase inhibitors to study aromatase activity in the brain and other tissues have been relatively, but inexplicably, unsuccessful.

SUMMARY OF THE INVENTION (S)-Vorozole (6-[(S)-(4-chlorophenyl)-1H-1,2,4-triazol-1-ylmethyl]-1-methyl-1H-benzotriazole) (structure 1) is a specific and potent non-steroidal aromatase inhibitor (Wouters, et al: (1989) J. Steroid. Biochem. Mol. Biol. 32:781-788; Decoster, et al. (1990) J. Steroid. Biochem. Mol. Biol. 37:335-341) originally developed as an antineoplastic agent (Decoster, et al. (1992) Cancer Res. 52:1240-1244).

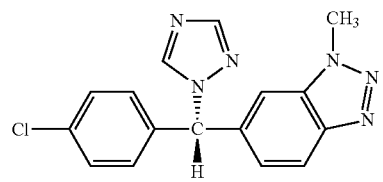

1

Standard synthetic routes to the preparation of vorozole racemic mixtures as well as methods for producing the enantiomeric (S) stereoisomer are well known. For example, see U.S. Pat. No. 4,943,574, the contents of which are incorporated herein by reference, DeKnaep, et al. (2000) Org. Process Res. & Devel. 4:162-166, and Venet, et al. (1997) Actualités de Chimie Therapeutique 23:239-246. These methods generally make use of N-1 methyl-benzotriazole and its derivatives as a starting material. Thus the methyl group in vorozole is located in the N-1 position of the benzotriazole ring.

To develop a route to preparing vorozole as a $^{11}$C positron emission tomography (PET) radiotracer it was practical to use $^{11}$C-methyl iodide to methylate a precursor compound lacking the N-1 benzotriazole methyl group. Thus norvorozole (S)-norvorozole (5-[(S)-(4-chlorophenyl)-1H-1,2,4,-triazol-1-yl)methyl]-1H-benzotriazole) (structure 2) was used as the precursor over a decade ago to make carbon-11 labeled vorozole via N-alkylation with [$^{11}$C]methyl iodide (Lidström, et al. (1998)) for positron emission tomography (PET) imaging and in vitro studies as a research tool for studies of aromatase in brain and peripheral organs.

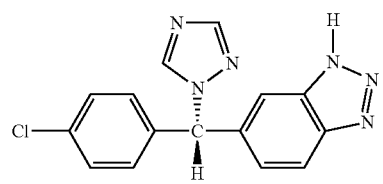

2

Lidström et al. (1998) reported that the alkylation reaction resulted in the formation of two isomers of vorozole, [N-methyl-$^{11}$C]vorozole, (i.e., the N-1 isomer, structure 3) and the N-3 isomer (structure 4) in a 5:2 ratio. They reported that $^{11}$C vorozole was well separated from the N-3 isomer under the HPLC conditions employed.

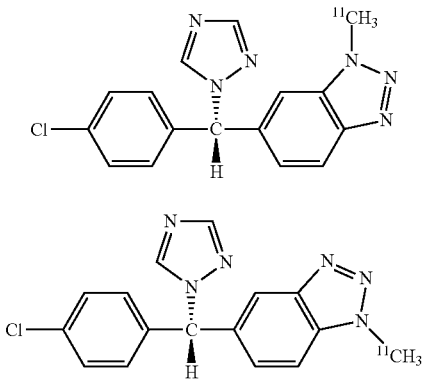

3

4

Despite the purported purity of the ([N-methyl-$^{11}$C]vorozole) synthesized by the Lidström et al. (1998) procedure, the radiotracer showed high liver uptake and "an otherwise relatively even distribution of radioactivity". They further found that blocking with unlabeled vorozole pretreatment caused only minor alterations of the biodistribution of the radiotracer. Takahashi, et al. (2006), using similar synthetic and apparently similar purification methods, found low target-to-background ratios (e.g. amygdala to cerebellum ratio of 1.25) and variability in blockable uptake in the preoptic area. However, the radiotracer showed remarkable metabolic stability in plasma and reasonable brain penetration.

In the present work, a mixture of compounds was also found upon reproducing the original synthesis and purification conditions for C-11 labeled vorozole. Furthermore, the labeled vorozole prepared as described by Lidström et al. (1998) showed low regional specificity and high non-specific binding in baboon brain imaging studies.

The imaging results with the labeled compound did not correlate well with the known specificity of pure vorozole, which, as noted herein is routinely synthesized using a precursor having the methyl group located at the N-1 position of the benzotriazole ring. The imaging results also failed to correlate with other methods that identified brain regions high in aromatase mRNA and aromatase activity (Abdelgadir, et al. (1997) Biol. Reprod. 57:772-777). Our laboratory's additional demonstration that [$^{11}$C]letrozole failed to provide a reliable radiotracer for aromatase activity, suggested that use of [$^{11}$C]-labeled aromatase inhibitors was less sensitive to levels of aromatase in vivo than the other, in vitro methods used to measure levels of aromatase. However, while not clarifying the reason for the poor results with [$^{11}$C]letrozole, an alternative explanation of our results and the earlier reports with [$^{11}$C]vorozole was that the fraction previously thought to be pure [$^{11}$C]vorozole could be a mixture of compounds.

A detailed investigation of the alkylation of norvorozole (structure 2) with both [$^{12}$C] and [$^{11}$C]methyl iodide, revealed that the original synthesis resulted in three isomers, not two isomers, and that the well separated labeled side product previously reported as the N-3 isomer was actually the N-2 isomer (structure 5).

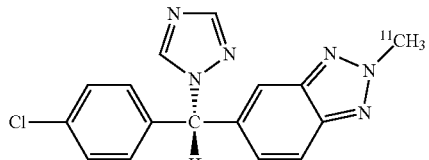

5

Moreover, under the reported HPLC conditions (Lidström, et al. 1998), the N-3 isomer (structure 4) co-eluted with [N-methyl-$^{11}$C]vorozole (the N-1 isomer, structure 3) and thus affected PET imaging and analysis.

The specific separation of pure [N-methyl-$^{11}$C]vorozole (N-1 isomer) from the heretofore unrecognized contaminating $^{11}$C labeled N-3 isomer resulted in a reliable and highly specific in vivo radiotracer for cytochrome P450 aromatase enzymes.

Thus, one form of the present invention is directed to N-1 radio-methyl vorozole (structure 6, wherein *C represents an isotope of carbon and [§]H represents an isotope of hydrogen) substantially separated from the N-3 radio-methyl isomer (structure 7, wherein *C represents an isotope of carbon and [§]H represents an isotope of hydrogen).

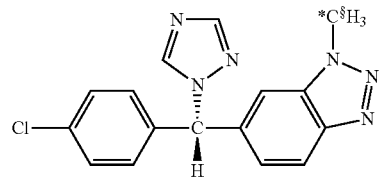

6

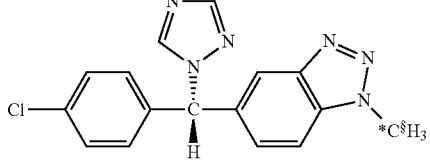

7

The radio-methyl labeled vorozole, substantially separated from the radio-methyl N-3 isomer, may be labeled with an isotope of carbon (*C), including carbon-11 ($^{11}$C), carbon-13 ($^{13}$C) and carbon-14 ($^{14}$C). Alternatively the radio-methyl labeled vorozole may be labeled with an isotope of hydrogen ([§]H), including deuterium (D) or tritium ($^3$H). Further, the radio-methyl labeled vorozole may be dual labeled with an isotope of carbon as well as an isotope of hydrogen or with a mixture of isotopes of carbon or with a mixture of isotopes of hydrogen and combinations thereof.

Another embodiment of the present invention includes the methods for substantial separation of radio-methyl vorozole from the radio-methyl N-3 isomer. The methods include analytical scale separation methods as well as preparative scale separation methods. The methods further include rapid methods useful in preparation of the $^{11}$C-labeled vorozole where time is of the essence as well as less rapid methods which may be useful for preparing radio-methyl labeled vorozole with the long-lived isotopes ($^{13}$C, $^{14}$C, D and $^3$H).

In addition this invention provides means for using the radio-methyl labeled vorozole, substantially separated from the radio-methyl N-3 isomer. The means of using the compound include its use in positron emission tomography (PET) ($^{11}$C labeled), magnetic resonance imaging (MRI) ($^{13}$C labeled), autoradiography in tissue sections ($^{14}$C labeled, and/or $^3$H labeled) and enzyme kinetics and mechanistic studies (D labeled).

DETAILED DESCRIPTION OF THE INVENTION

Reinvestigation of the synthesis and purification of [N-methyl-$^{11}$C]vorozole showed that all three benzotriazole isomers (vorozole, i.e., N-1 (structure 3); N-2 (structure 5); and N-3 (structure 4)) are produced. Each of the isomers was characterized by $^{13}$C-NMR and by 2D-NOESY spectra. A rapid HPLC system to substantially separate [N-methyl-$^{11}$C] vorozole from the [$^{11}$C]labeled N-3 isomer (structure 3) using a pentafluorophenylpropyl bonded silica HPLC column was developed. Positron emission tomography (PET) studies in non-human primates of the pure [N-methyl-$^{11}$C]vorozole revealed accumulation of C-11 in all brain regions with highest accumulation in the aromatase rich amygdala and preoptic area (POA). Accumulation in these brain regions as well as other brain regions could be blocked by pretreatment with vorozole or letrozole, in accordance with reports indicating that some level of aromatase expression is present in many brain regions.

The significant image degradation caused by the contamination of the labeled vorozole (structure 3) with an equal amount of the N-3 isomer (structure 4) brings to light the fact that [N-methyl-$^{11}$C]vorozole, substantially separated from the [$^{11}$C] N-3 isomer, will be a significantly better radiotracer than earlier studies had indicated. These findings necessitate the re-evaluation [N-methyl-$^{11}$C]vorozole data from previous studies, both in vivo and in vitro. The availability of pure [N-methyl-$^{11}$C]vorozole for PET represents a new scientific tool for studies of the biology of aromatase and for drug research and development.

An initial research goal was to reproduce the previous radiosynthesis and HPLC conditions (observation of two radioactive fractions) and then to separate the "vorozole" fraction (X) if it was found that it comprised a mixture of vorozole and another isomer as suggested in trial results with non-radioactive methyl iodide. Since the HPLC column (Spherisorb ODS1, Beckman, 250 mm×10 mm) used previously was not commercially available, it was replaced with a similar HPLC column (Spherisorb ODS (2), Phenomenex, 5μ, 250 mm×10 mm).

Figure 1:
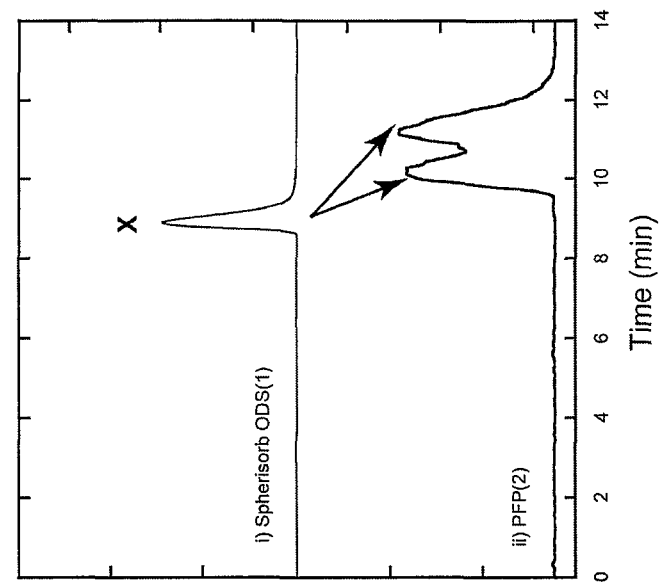
FIG. 1: A. Preparative HPLC profile of the crude reaction mixture from the alkylation of norvorozole with [$^{11}$C]methyl iodide. HPLC conditions: Spherisorb ODS (2) (Phenomenex, 5μ, 250 mm×10 mm); eluent, ammonium formate buffer (50 mM, pH 3.5):acetonitrile (65:35), 5 mL/min. Fraction X was isolated and subjected to analytical HPLC. B. Comparison of HPLC analysis of the isolated "vorozole" fraction X, in the Lidström, et al. (1998) system (top graph: Spherisorb ODS (1), (Phenomenex, 5μ, 250×4.60 mm); eluent, ammonium formate buffer (50 mM, pH 3.5):acetonitrile (40:60), 1 mL/min) and in the new HPLC system (lower graph: Luna PFP(2), (Phenomenex, 5μ, 250 mm×4.6 mm); eluent, aqueous formic acid (pH 3.0):methanol (1:2), 1 mL/min).
Figure 1:
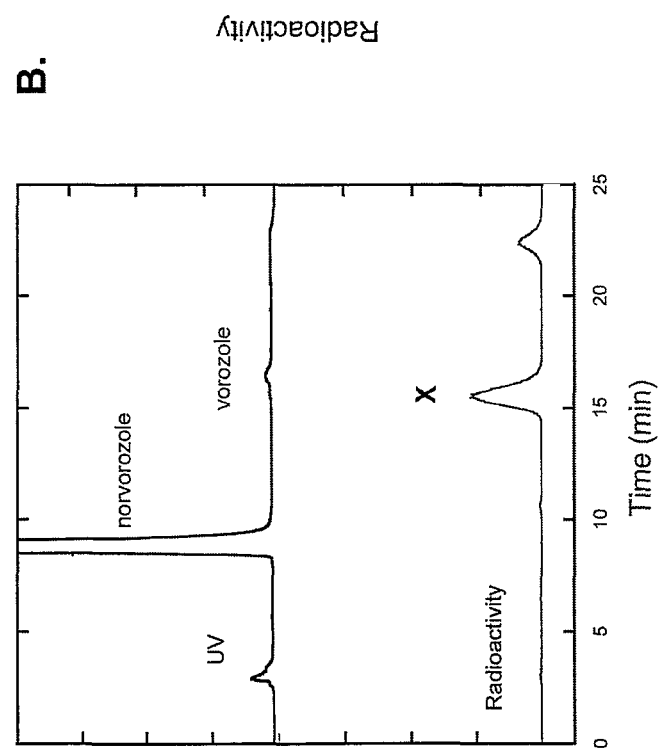

Using this HPLC column only two radioactive fractions in a ratio of 2:1 were observed. The major radioactive fraction X (retention time 15 minutes) (FIG. 1A), which has the same retention time as authentic vorozole, was isolated and subjected to further separation analysis (FIG. 1B) using analytical HPLC systems. A similar HPLC column (Spherisorb ODS (1), Phenomenex, 5μ, 250×4.60 mm) to that reported previously (Lidström, et al. 1998) failed to reveal any heterogeneity in X as it showed only one peak in this system (FIG. 1B, upper graph). Many other conventional ODS columns gave the same results using various solvent systems.

However, a pentafluorophenylpropyl (PFPP) bonded-phase HPLC column resolved the 15 min fraction X into two peaks having the same retention times as a preparation of unlabeled N-3 isomer (structure 4) and as vorozole (structure 1 and 3) (FIG. 1B, lower graph).

Figure 2:
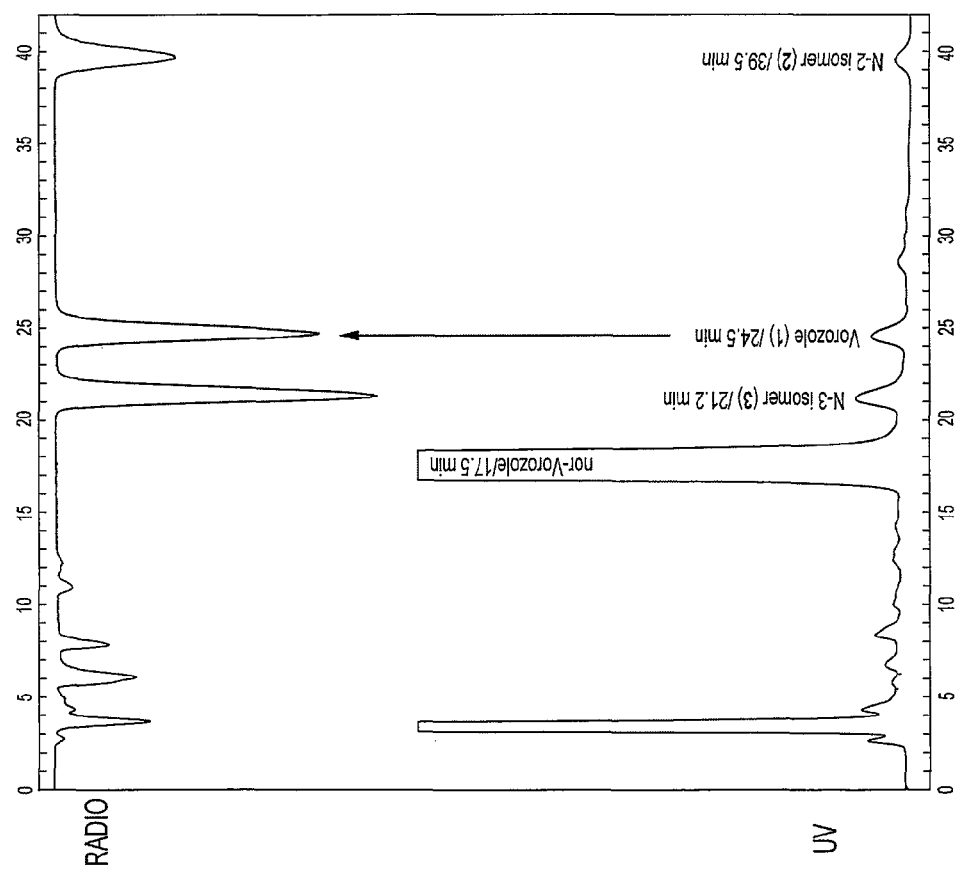
FIG. 2: Preparative HPLC profile of the crude reaction mixture from the alkylation of norvorozole with [$^{11}$C]methyl iodide. Baseline separation of [N-methyl-$^{11}$C]vorozole from the N-2 and N-3 isomers was achieved. HPLC conditions: Luna PFP(2) (Phenomenex, 250 mm×10 mm, 5μ); aqueous formic acid adjusted to pH=3)/methanol (45/55); 5 ml/min.

All three isomers of the crude reaction mixture were well-separated using a semi-preparative scale PFPP column (FIG. 2). The radiochemical yields of the three isomers were approximately 30% each. The radiochemical purity was >97% and the specific activity ranged 10-19 Ci/μmol (0.3-0.7 GEq/μmol). The total radiosynthesis and separation time was 65 min after the end of the cyclotron bombardment (EOB).

In one embodiment, radio-methyl vorozole, substantially separated from the radio-methyl N-3 isomer of vorzole is provided. The radio-methyl vorozole, substantially separated from the radio-methyl N-3 isomer of vorzole, may contain a radioisotope of carbon. The radioisotope of carbon may be $^{11}$C, $^{13}$C or $^{14}$C. The radio-methyl vorozole, substantially separated from the radio-methyl N-3 isomer of vorzole, may contain a radioisotope of hydrogen. The radioisotope of hydrogen may be deuterium (D) or tritium ($^3$H). The radio-methyl vorozole, substantially separated from the radio-methyl N-3 isomer of vorzole, may contain a mixture of isotopes, including a mixture of isotopes of carbon, a mixture of isotopes of hydrogen and/or a mixture of isotopes of hydrogen and isotopes of carbon.

Radio-methyl vorozole, substantially separated from the radio-methyl N-3 isomer, is a preparation of radio-methyl vorozole that comprises greater than 50% mole fraction radio-methyl vorozole and less than 50% mole fraction N-3 isomer. Preferably radio-methyl vorozole, substantially separated from the radio-methyl N-3 isomer, is a preparation of radio-methyl vorozole that comprises greater than 70% mole fraction radio-methyl vorozole and less than 30% mole fraction N-3 isomer. More preferably radio-methyl vorozole, substantially separated from the radio-methyl N-3 isomer, is a preparation of radio-methyl vorozole that comprises 90% or greater mole fraction radio-methyl vorozole and 10% or less mole fraction N-3 isomer.

Isomers of vorozole, i.e., vorozole, in which the methyl group is at the N-1 position of the benzotriazole ring; the N-2 isomer in which the methyl group is at the N-2 position of the benzotriazole ring; and the N-3 isomer in which the methyl group is at the N-3 position of the benzotriazole ring may be designated variously as isomers, topoisomers and/or regioisomers and each designation is intended to convey the same meaning.

Methods of preparing radio-methyl vorozole, substantially separated from the radio-methyl N-3 isomer, include analytical scale and preparative scale chromatographic procedures.

Substantial separation of vorozole from the N-3 isomer of vorozole makes use of high performance liquid chromatography resins that provide multiple mechanisms for selectivity. The resins for substantial separation of the isomers provide a combination of at least two mechanisms for selectivity including hydrogen bonding, dipole-dipole interaction, aromatic Π-Π interaction and hydrophobic interaction. Many such resins are well known in the art and generally may include, variously, aromatic groups, alkyl groups and halogen groups to facilitate the combination of separation mechanisms. One example used in the present study was the pentafluorophenylpropyl-bonded Luna® PFP, which afforded a rapid substantial separation of the vorozole from the N-3 isomer.

Another example used in the present study was phenoxypropyl bonded column (Synergi™ PolarRP) which afforded a less rapid, but substantial separation of vorozole from the N-3 isomer. In the pheonxypropyl column separation the retention times for both isomers was greater than 50 minutes using aqueous formic acid (pH=3.5):methanol (50:50) as the eluent. This latter resin may be suitable for separation of radio-methyl vorozole from the radio-methyl N-3 isomer when long lived radioisotopes ($^{13}C$, $^{14}C$, $^{3}H$ and D) are used.

While the systems demonstrated here to substantially separate radio-methyl vorozole from the radio-methyl N-3 isomer were reverse phase high performance liquid chromatography systems, it is possible that normal phase high performance liquid chromatography systems may be developed to provide suitable combinations of hydrogen bonding, dipole-dipole interaction, aromatic Π-Π interaction and hydrophobic interaction to effect the separation.

An analytical scale procedure may include two chromatography steps. The method includes providing of a reaction mixture for methyl-labeling of norvorozole comprising norvorozole and radio-methyl iodide, wherein radio-methyl iodide ($*C^{\S}H_3I$) contains either isotopes of carbon ($*C$) or isotopes of hydrogen ($^{\S}H$) or mixtures thereof, a first chromatography step to separate a mixture comprising the radio-methyl vorozole and the radio-methyl N-3 isomer from the radio-methyl N-2 isomer and a second chromatography step to substantially separate radio-methyl vorozole from the radio-methyl N-3 isomer.

In this two step analytical procedure, the first chromatography step may be performed on a number of HPLC chromatographic supports using a variety of conditions. Conventional ODS columns may be used interchangeably to effect the separation of the N-1, N-3 mixture of isomers from the N-2 isomer. A support of Spherisorb ODS with an ammonium formate buffer (50 mM, pH 3.5):acetonitrile (65:35) eluent provides a mixture of radio-methyl vorozole and the radio-methyl N-3 isomer separated from the radio-methyl N-2 isomer.

The second chromatography step to separate radio-methyl vorozole from the radio-methyl N-3 isomer makes use resins having multiple mechanisms of selectivity and which provide a combination of mechanisms of separation. Such resins generally include combinations of one or more of aromatic groups, halogen groups and alkyl groups. A pentafluorophenylpropyl (PFPP) bonded silica column may be used. A Luna PFP (2) support may be used with an aqueous formic acid (pH 3):methanol (1:2) eluent.

Alternatively, the second chromatography step to separate radio-methyl vorozole from the radio-methyl N-3 isomer may make use of Synergi™ Polar RP with aqueous formic acid (pH=3.5):methanol (50:50) as the eluent.

Preferably, analytical or preparative scale separation methods may involve a single high performance liquid chromatography procedure to separate radio-methyl vorozole from the N-2 and the N-3 radio-methyl isomers. The method includes provision of a reaction mixture for methyl-labeling of norvorozole comprising norvorozole and radio-methyl iodide. Following the labeling reaction, the mixture is subjected to chromatography on an HPLC resin offering multiple mechanisms for selectivity and therefore, a combination of separation mechanisms. Such resins generally are comprised of aromatic groups (e.g., phenyl) and halogen groups (e.g., fluorine) and alkyl groups (e.g., propyl, butyl, hexyl, dodecyl, octadecyl, etc.). Examples of such resins include pentafluorophenylpropyl (PFPP) bonded silica resins, such as Luna PFP(2). The eluent is comprised of aqueous formic acid (pH 3):methanol mixtures in ratios from about 1:1 to about 1:2 and preferably about 1:1.5.

Radio-methyl vorozole, substantially separated from the N-3 radio-methyl isomer, may be used in a variety of studies. When the compound is labeled with the positron emitting $^{11}C$ atom, the compound is suitable for imaging aromatase in living systems using positron emission tomography (PET). Preparation of the [N-methyl $^{11}C$] vorozole, substantially separated from the [$^{11}C$]-N-3 isomer, for use in such studies includes removal of the HPLC solvent, for example by evaporation, followed by resuspension of [N-methyl $^{11}C$] vorozole, substantially separated from the N-3 isomer, in a suitable aqueous solution, for example physiological saline and sterilization, for example by filtration.

Animal subjects are prepared for PET imaging using well known procedures. Catheters may be inserted in a suitable artery and a vein for arterial sampling and radiotracer injection respectively. Dynamic PET imaging may be carried out using commercially available PET cameras and associated data collection systems, analyzing equipment and software. Doses of [N-methyl $^{11}C$] vorozole may range from about 1 to about 5 mCi, with a specific activity ranging from about 10 to about 25 Ci/µmol with an injected mass ranging from about 0.05 to about 0.5 nmol. Dynamic scanning is carried out for a suitable period of time, generally 30 to 90 minutes. Arterial sampling may be performed to obtain the time activity curve in plasma and to analyze selected samples for the fraction of C-11 present as unchanged parent compound. During the PET scan, subjects are monitored for heart rate, respiration rate, $PO_2$ and temperature.

The PET imaging may be whole body imaging of the subject animal. Alternatively the PET imaging may be limited to a specific portion of the body of the imaged subject. A specific portion of the body of the imaged subject may be the brain, and/or specific sub-structures thereof; various glands of the subject, including adrenal glands, pituitary glands, ovaries and testes; the lymphatic system of the subject, including the lymph nodes; the pulmonary system, including the lungs and heart; various organs, including the liver and kidneys; and, where the subject animal is a mammal, the breasts.

The results of the PET imaging studies may be used for assessment of the efficacy of reduction of aromatase activity in subjects, for example, breast cancer patients treated with aromatase inhibitors. Displacement or blockade of [N-methyl $^{11}C$] vorozole from binding aromatase by pre-administration of varying dosages of known or new aromatase inhibitors can be used to assess the efficacy and dose requirements of the aromatase inhibitors. This is useful in the development of new drugs to inhibit aromatase in patients with estrogen-sensitive cancers.

In such procedures to determine the efficacy of a dose of an aromatase inhibitor, generally a target tissue is selected for imaging the binding of the radiotracer [N—$^{11}$C-methyl]vorozole (substantially separated from the N-3 radio-methyl isomer) and a baseline PET scan is obtained after injection of the radiotracer. After the $^{11}$C has been allowed to decay for three to ten, or more, half-lives (e.g., one to six hours), a challenge dose of the aromatase inhibitor is administered at a predetermined period of time prior to a second injection of the radiotracer [N—$^{11}$C-methyl]vorozole (substantially separated from the N-3 radio-methyl isomer) is administered and a second PET scan is obtained. The efficacy of the aromatase inhibitor and efficacy of the specific dose administered can be assessed by comparing the images from the baseline scan (first scan) with the images in the challenge scan (second scan) to determine how well or poorly the challenge dose diminished binding by the radiotracer.

Because aromatase enzymes are also located in the brain, particularly in the amygdala and the preoptic area of non-human primates, [N-methyl $^{11}$C] vorozole, substantially separated from the N-3 isomer, is useful for PET imaging assessment of the activity levels of aromatase in relationship to estrogen effects on neuronal health. It is potentially useful as a tracer for changes in aromatase in the brain that occur during (or as a result of) the development of Alzheimer's disease. It is further useful for studies examining the role of estrogens in neuro-protection following brain injury.

When [N-methyl $^{13}$C] vorozole, substantially separated from the N-3 isomer, is prepared it may be used in Magnetic Resonance Imaging (MRI) scans of subjects. Preparation for injection into a subject is as described for the [N-methyl $^{11}$C] vorozole, including resuspension in an aqueous medium and sterilization. Although such studies remain to be performed it is likely that MRI of vorozole in animals will be useful for examination of brain responses to brain injury and in studying neurodegenerative diseases, such as Parkinson's disease and Alzheimer's.

When [N-methyl $^{14}$C] vorozole or [N-methyl $^{3}$H] vorozole, substantially separated from the radio-methyl N-3 isomer, are prepared they may be used for autoradiographic experiments on tissue sections using standard methods well known in the art. The location of aromatase enzymes within preserved tissue samples can be determined using a combination of autoradiography and microscopy.

In such studies, suitable tissue preparations include breast biopsies, brain biopsies and other tissue specimens. Such tissues may be flash frozen and sectioned for slide preparation or may be preserved (e.g., in formalin or other preservative solvent) and then sectioned for slide preparation. The tissue sections are then incubated with [N-methyl $^{14}$C] vorozole or [N-methyl $^{3}$H] vorozole, substantially separated from the radio methyl N-3 isomer, under conditions suitable for binding of the aromatase enzymes in the tissue preparation. Following incubation, the tissue preparation is washed to remove excess labeled vorozole and an image is obtained using autoradiography, for example, using photographic film, phosphor imaging or a beta-imager. These results can then be correlated to the gross anatomy derived from histological staining as well as micro-structure of the tissue examined using microscopy.

When [N-methyl D] vorozole, substantially separated from the N-3 isomer is prepared, it may be used for in vitro examination of the mechanism of the inhibition of isolated aromatase enzymes by vorozole. It may further prove useful for studies examining the mechanism of interaction of other aromatase inhibitors with the enzyme active site.

EXEMPLIFICATIONS

General Methods

Vorozole and norvorozole, and their enantiomers were generously provided by Johnson & Johnson Pharmaceutical Research and Development (Beerse, Belgium). All other chemicals and solvents were purchased from Aldrich Chemical Company (Milwaukee, Wis., USA) and were used without further purification.

NMR spectra were recorded using a Bruker Avance 400 MHz NMR spectrometer (Bruker Instruments Inc. Billerica, Mass., USA). GC-MS analyses were performed with an Agilent 6890/5973N GC/MSD system (Agilent Technologies, Avondale, Pa., USA) equipped with a DB-5 column (30 m length×0.250 mm ID, 5 µm film thickness; injector temperature; split; injection temperature, 280° C.; oven temperature, 280° C., isothermal; carrier gas, He; flowrate 1 mL/min). The temperature of source and quadrupole of mass spectrometer were 280° C., 180° C., respectively.

[$^{11}$C]Methyl iodide was produced using a PETtrace MeI Microlab (GE Medical Systems, Milwaukee, Wis., USA) from [$^{11}$C]carbon dioxide, which was generated from a nitrogen/oxygen (1000 ppm) target ($^{14}$N (p,α)$^{11}$C) using EBCO TR 19 cyclotron (Advanced Cyclotron Systems INC. Richmond, Canada). High performance liquid chromatography (HPLC) purification was performed by a Knauer HPLC system (Sonntek Inc., Woodcliff Lake, N.J., USA) with a model K-5000 pump, a Rheodyne 7125 injector, a model 87 variable wavelength monitor, and NaI radioactivity detector.

During the radiosynthesis, C-11 was measured by three PIN diode detectors (3×3 mm Si diode, Carroll Ramsey Associates, Berkeley, Calif.) equipped with a triple-channel amplifier (model 101-HDC-3; Carroll Ramsey Associates, Berkeley, Calif.) and NI USB-6008 (National Instruments, Austin, Tex.). Radioactivity of [N-methyl-$^{11}$C]vorozole was measured by a Capintec CRC-712MV radioisotope calibrator (Capintec Inc., Ramsey, N.J., USA). $^{11}$C Radioactivity of preparative HPLC samples was measured by a Packard MINAXI γ 5000 automated gamma counter (Packard Instrument, Meriden, Conn.). All radioactivity measurements were decay-corrected. Specific activity was measured by radioactivity/mass (Ci/µmol). For quality control, radiochemical purities were measured by analytical HPLC using aqueous formic acid solution (0.1% (v/v), pH=2.8):methanol (1:2) at a flow rate 1 mL/min on a Luna PFP(2) (250 mm×4.6 mm, 5µ; Phenomenex, Torrance, Calif.). For baboon PET studies, a formulation of [N-methyl-$^{11}$C]vorozole (and the N-1/N-3 mixture and the methyl [$^{11}$C] N-3 or N-2 isomers) in 4 mL of saline was used.

Analysis of reaction products from the reaction of norvorozole with unlabeled methyl iodide: Potassium carbonate (60 mg, 434 µmol) and methyl iodide (180 mg, 0.8 mmol) were added to a solution of (S)-norvorozole (6-[(S)-(4-chlorophenyl)-1H-1,2,4-triazol-1-ylmethyl]-1H-Benzotriazole (structure 2), 1.3 mg, 4 µmol) in anhydrous acetonitrile (1 mL). The reaction mixture was stirred at room temperature for 7 min. After evaporation of acetonitrile and excess of methyl iodide under reduced pressure, the crude product was extracted with ethyl acetate and dried with anhydrous sodium sulfate, filtered, and then evaporated to dryness using a rotary evaporator under reduced pressure. This crude mixture was separated by HPLC using aqueous formic acid solution (pH=3.0): methanol (45:55) at a flow rate 1 mL/min on a Luna PFP(2)

(250 mm×4.6 mm, 5µ; Phenomenex, Torrance, Calif.). The three major fractions of UV active peaks (N-3 isomer (structure 4, without $^{11}$C), $T_R$=21 min; vorozole (structure 1) $T_R$=24 min; N-2 isomer (structure 5, without $^{11}$C), $T_R$=35 min) were collected separately (ratio, 1:1:1), and evaporated under reduced pressure. The residual water was extracted with ethyl acetate, dried with anhydrous sodium sulfate, filtered, and evaporated to give three analytical samples. These samples were examined by $^1$H and $^{13}$C NMR.

Reaction of norvorozole with [$^{11}$C]methyl iodide: To (S)-norvorozole (structure 2, 1 mg, 3.22 pmol) in DMSO (300 µL) 5 M KOH (1 µL, 1.6 eq) was added. After vortexing for 30 sec, the reaction mixture was transferred into a 1.5 mL V-shape reaction vessel. [$^{11}$C]methyl iodide was transferred in a helium stream from the PETtrace MeI Microlab methyl iodide system into this solution at room temperature and peak trapping was observed by a pin-diode detector. After the vessel was heated to 90° C. for 3 min, the reaction mixture was cooled and diluted with HPLC eluent (1 mL). Preparative HPLC was performed using a method simulating the original publication method for the synthesis of [N-methyl-$^{11}$C]vorozole (Method A) and another to substantially separate [N-methyl-$^{11}$C]vorozole from the N-3 and N-2 isomers (Method B).

Method A (Partial Separation):

We slightly modified the original HPLC method of Lidström, et al. (1998) based on column availability. Briefly, the reaction mixture diluted with HPLC solvent (1 mL) was subjected to HPLC chromatography on a Spherisorb ODS2 (Phenomenex, 250×10 mm, 5µ) column using aqueous ammonium formate solution (50 mM, pH=3.5):acetonitrile (65:35), and a flow rate of 5 mL/min. The major C-11 labeled fraction (fraction X, FIG. 1A) was collected at the expected retention time ($T_R$=15 min) for vorozole and the other minor radioactive fraction was collected at 22 min. The 15 and 22 minute fractions were present in a ratio of about 2 to 1, respectively. The solvent was removed from the 15 minute fraction and it was rechromatographed on a pentafluorophenylpropyl (PFPP) based column (Luna PFP(2), Phenomenex, 250×0.46 mm, 5µ) column with aqueous formic acid (0.1% (v/v, pH=2.8):methanol (1:2) and flow rate of 1 mL/min to reveal two peaks of equal radioactivity at 10 and 11 min (FIG. 1B).

Method B (One-Step, Complete Separation):

The crude product in DMSO was diluted with HPLC solvent (1 mL) and chromatographed using a solvent mixture of aqueous formic acid solution (0.1% (v/v), pH=2.8):methanol (45:55) at a flow rate 5 mL/min on a Luna PFP(2) column (Phenomenex, 250 mm×10 mm, 5µ). [N-methyl-$^{11}$C]vorozole eluted at 24.5 min and was collected.

The HPLC solvent was removed by azeotropic evaporation with acetonitrile using a rotary evaporator under the reduced pressure. The residue was taken up by saline (4 mL), filtered through a 0.2 µm HT Tuffryn® membrane filter (Acrodisc® 25 mm Syringe Filter, Pall Life Sciences, Ann Arbor, Mich.) into a sterile vial ready for the baboon study. The radiochemical purity for [N-methyl-$^{11}$C] vorozole was >99% as determined by TLC (solvent, acetonitrile:water:NH$_4$OH (conc.) (90:9:1) on Macherey-Nagel plastic back silica plates ($R_f$: 0.6).

In separate syntheses, fractions containing the N-3 and the N-2 isomers (which eluted at 21.2 and 39.5 min, respectively) were collected.

Measurement of log D: Log $D_{7.4}$ for the three $^{11}$C isomers was measured using a published method (Ding et al. (2005) J. Neurochem. 94:337-351; Reichel, et al. (1998) Pharm. Res. 15:1270-1274). Briefly, an aliquot (50 µL) of the $^{11}$C vorozole or isomer solution was introduced into a mixture of 1-octanol (2.5 mL) and phosphate buffered saline (PBS, pH 7.4; 2.5 mL). The mixture was vortexed for 2 min and then centrifuged at 7000 rpm for 2 min. An aliquot (0.1 mL) of the clear octanol layer and 1.0 mL of the buffer layer were sampled separately into two empty vials and the amount of radioactivity was determined. Two mL of the octanol layer was transferred into a test tube containing 0.5 mL of fresh octanol and 2.5 mL of buffer. After vortexing and centrifuging in the same way as the first measurement, radioactivity of the second batch was measured. In general, these processes were repeated up to 6 times. Log $D_{7.4}$ at pH=7.4. is as the log$_{10}$ of the average of the ratios of the decay corrected counts in the octanol:phosphate buffer (pH=7.4).

Measurement of free fraction in plasma: An aliquot of each of the $^{11}$C-labeled isomers was incubated at room temperature for 10 min with baboon plasma (500 µL) as described previously (Ding, et al. (2005)). Briefly, aliquots (20-40 µL) of the incubated spiked plasma were counted (unspun aliquots). A portion of the incubation mixture (200-400 µL) was centrifuged using a Centrifree tube (Amicon Inc, Beverly, Mass., USA, molecular weight cut-off, 30,000) for 10 minutes. The top portion of the Centrifree tube (the bound portion) was removed and precisely measured aliquots (20-40 µL) of the liquid in the cup (unbound fraction) were counted. The free fraction is the ratio of radioactivity of the unbound aliquots to the radioactivity of the unspun aliquots. All counts were decay-corrected.

PET Studies in Baboons: All animal studies were reviewed and approved by the Brookhaven Institutional Animal Care and Use Committee. Four different baboons were studied in 7 PET sessions where two or three radiotracer injections were administered two hours apart to compare different isomers or to assess reproducibility of repeated measures or the effects of a blocking dose of vorozole or letrozole (0.1 mg/kg, 5 min prior). Baboons were anesthetized with ketamine (10 mg/kg) and then intubated and ventilated with a mixture of isoflurane (Forane, 1-4%) and nitrous oxide (1500 mL/min) and oxygen (800 mL/min). Animals were transported to and from the PET facility in a temperature controlled transfer cage and a member of the staff attended them while they recovered from anesthesia. Catheters were inserted in a popliteal artery and radial arm vein for arterial sampling a radiotracer injection respectively. Dynamic PET imaging was carried out on a Siemen's HR+ high resolution, whole body PET scanner (4.5×4.5×4.8 mm at center of field of view) in 3D acquisition mode, 63 planes. A transmission scan was obtained with a $^{68}$Ge rotating rod source before the emission scan to correct for attenuation before each radiotracer injection. The injected dose of $^{11}$C compounds ranged from 55.5 to 185 MBq, the specific activity ranged from 16 to 19 Ci/µmol at the end of the bombardment and the injected mass ranged from 0.08-0.3 nmol. Dynamic scanning was carried out for 90 minutes with the following time frames (1×10 sec; 12×5 sec; 1×20 sec; 1×30 sec; 8×60 sec; 4×300 sec; 8×450 sec). Arterial sampling was performed to obtain the time activity curve in plasma and to analyze selected samples for the fraction of C-11 present as unchanged parent compounds with the sample times described previously (Ding, et al. (2005)). During the PET scan, baboons were monitored for heart rate, respiration rate, PO$_2$ and temperature. Animals were allowed 4 weeks between studies to recover from anesthesia and blood sampling.

Plasma analysis for fraction of $^{11}$C-isomers: Plasma samples at 1, 5, 10, 30 and 60 min were analyzed by HPLC to determine the percent of residual parent tracer. Plasma samples from selected time points were added to 300 µL acetonitrile containing an appropriate amount of standard, then subjected to cell disruption using a Polytron (Brinkmann Instruments), centrifuged for 4 minutes and decanted into 300 µL water. HPLC conditions were 60:40 0.1 M ammonium formate:acetonitrile, Waters µBondapak column (3.9×300 mm), flow 1.3 mL/min, UV detection at 254 nm. Supernatants were injected onto the column, reserving a measured amount to determine recovery of injected activity from the column. Retention times were 7.5 minutes for vorozole itself and the N-3 isomer, and 9.5 minutes for the N-2 isomer. Five fractions were collected from each injection, 3 before the parent peak, the parent peak, and finally the tail of the parent peak. The percent unchanged tracer was determined by dividing the sum of the last 2 peaks by the sum of all HPLC fractions. Sample recoveries were determined to verify that there were no labeled metabolites retained on the column.

Image Analysis: Time frames were summed over the 90 minute experimental period. Regions of interest were placed over the amygdala, the preoptic area, frontal cortex, cerebellum and thalamus on the summed image and then projected onto the dynamic images to obtain time activity curves. Regions occurring bilaterally were averaged. Carbon-11 concentration in each region of interest was divided by the injected dose to obtain the % dose/cc. The summed PET images from one baboon was co-registered with a 3D MR image of the same animal using PMOD (PMOD Technologies, Ltd.).

Results and Analysis:

Reaction of norvorozole (structure 2) with [$^{12}$C]methyl iodide: Because [N-methyl-$^{11}$C]Vorozole synthesized by the published method (Lidström, et al, 1998) using slightly modified HPLC purification conditions, did not give the high signal to noise baboon brain images and because autoradiography results with rat brain sections also showed non-specific binding, we examined the products of the Lidström et al. (1998) reaction and purification methods more thoroughly using unlabeled methyl iodide.

Given the alkaline reaction medium, we first considered whether the non-specific binding could be a result of racemization, resulting in the formation of the inactive (R)-vorozole (Wouters, et al. (1990) J. Steroid. Biochem. Mol. Biol. 37:1049-1054), which would have co-eluted with the active form. However, chiral HPLC analysis (column, Chiralpak OJ-P, 4.6×15 mm; eluent, water:acetonitrile (75:35); flow-rate, 0.5 ml/min) indicated that no racemization of either (S)-norvorozole or (S)-vorozole occurred under the reaction conditions.

Serendipitously, during this investigation, we uncovered the presence of an unexpected reaction product, was formed in approximately equal yield to (S)-vorozole. This product was not separable under the HPLC conditions originally reported. Thus Lidström et al. (1998) noted only two major fractions "in a ratio of 5 to 2". The authors identified the two fractions as ([N-methyl-$^{11}$C]vorozole (N-1 alkylation) and an isomer, (N-3 alkylation isomer). Their assignment was based on $^{13}$C NMR experiments, in which [$^{13}$C]methyl iodide was added as a carrier in the carbon-11 methylation reaction in order to have sufficient mass for a $^{13}$C NMR. After HPLC isolation of the fraction with the expected retention time of vorozole, the authors determined the chemical shift of the $^{13}$C-enriched product matched that of vorozole (34.4 ppm). The Lidström, et al. (1998) minor isomer, which was well separated under their HPLC conditions, was also isolated and analyzed by $^{13}$C NMR and assigned as the N-3 methylation product with a reported chemical shift of 43.4 ppm.

When we reproduced the original radiosynthesis as closely as possible (Spherisorb ODS2 columns (Phenomenex) were used instead of Spherisorb ODS1 (Beckman) because of commercial availability), we also found two apparent C-11 labeled fractions in a similar ratio (2:1) (FIG. 1A).

Since there was precedent for alkylation at the N-2 position of benzotriazole rings (Kopanska et al. (2004) Bioorgan. Med. Chem. 12:2617-2624), we investigated the possibility that the N-2 isomer may have formed and that it co-eluted with the labeled vorozole, thus accounting for the low specificity and reproducibility we had observed in our PET studies. In fact, GC-MS analysis confirmed that three products were formed by the reaction of norvorozole with excess methyl iodide. Consistent with our hypothesis, each of the three isomers had the same molecular weight ($M^+$=324) yet their fragmentation patterns differed distinctly. Later, we observed three singlet peaks between 4.2-4.6 ppm in the $^1$H-NMR spectrum. The $^{13}$C-NMR spectrum of the crude reaction mixture also confirmed three methyl peaks, 34.61, 34.66, and 43.64 ppm. Thus, it was apparent that the reaction mixture contained three different methylated compounds.

In spite of rigorous HPLC analysis with six different reversed-phase and two different normal-phase columns using several gradient elution systems, only two major fractions were observed. This prompted us to isolate and characterize the two major UV-active fractions from HPLC separation in order to confirm that the vorozole fraction was contaminated by one of the other isomers.

GC-MS and $^{13}$C-NMR analysis of the fraction assigned as vorozole confirmed the presence of two isomers of the same molecular weight with $^{13}$C-methyl shifts of 34.61 and 34.66 ppm (125 MHz, CDCl$_3$), one of which (34.61 ppm) corresponded to the chemical shift of an authentic sample of vorozole. These two shifts are so similar that they were probably not resolved at the lower field strength used in the original analysis (Lidström, et al. 1998). Thus the Lidström et al. (1998) rigorous analysis, which has been typical in the field of carbon-11 labeling radiosynthesis was, in this instance, unable to distinguish the two isomers and thus led to PET evaluation of a mixture, with concomitantly poor results.

Complete resolution of the reaction mixture: To achieve the exceptionally difficult separation of the three isomers for full characterization, we screened a number of methods for purification. An initial separation of the two co-eluting isomers from the ODS column was achieved ($T_R$=52 and 58 min) using aqueous formic acid (pH=3.5)/methanol (50:50) at a flow rate (1 mL/min) on a silica based phenoxypropyl bonded column (Synergi™ PolarRP, 5µ, 250×4.6 mm, Phenomenex). After isolation, each compound was characterized by $^{13}$C-NMR and 2D-NOESY NMR.

The byproduct that could be isolated in pure form using the original ODS HPLC conditions ($^{13}$C of N-methyl, 43.64 ppm), and which was previously assigned as the N-3 methylated isomer (structure 4), was re-assigned as the N-2 isomer (structure 5). This reassignment was primarily based on the $^{13}$C chemical shift of the two quaternary carbons (both C-8 and C-9, above 140 ppm) of the benzoquinoid ring, which were shifted clearly downfield relative to the corresponding one of benzotriazole carbons which is typically below 140 ppm (Carta, et al. (2005) Heterocycles 65:2471-2481).

The other two isomers, which co-eluted under the original HPLC conditions but which were separated by the Synergi™ PolarRP column and then by the PFPP column, were identified as vorozole (N-1 isomer, structure 3) and the N-3 isomer (structure 4). Their structural assignments were largely based on the NOE (nuclear Overhauser effect) correlation of the H-7 or H-4 to the methyl group.

Comparison of C-11 labeled [N-methyl-$^{11}$C]vorozole and the $^{11}$C-labeled N-2 and N-3 isomers and a mixture of [N-methyl-$^{11}$C]vorozole and $^{11}$C-labeld N-3 isomer in the baboon brain: All three regioisomers have a lipophilicity (log $D_{7.4}$) considered suitable for blood-brain barrier penetration. Notably, the log D's of vorozole and the N-3 isomer were almost identical, which is consistent with their co-elution on HPLC using the ODS column. The free fraction of the two isomers in baboon plasma was also similar.

Figure 3:
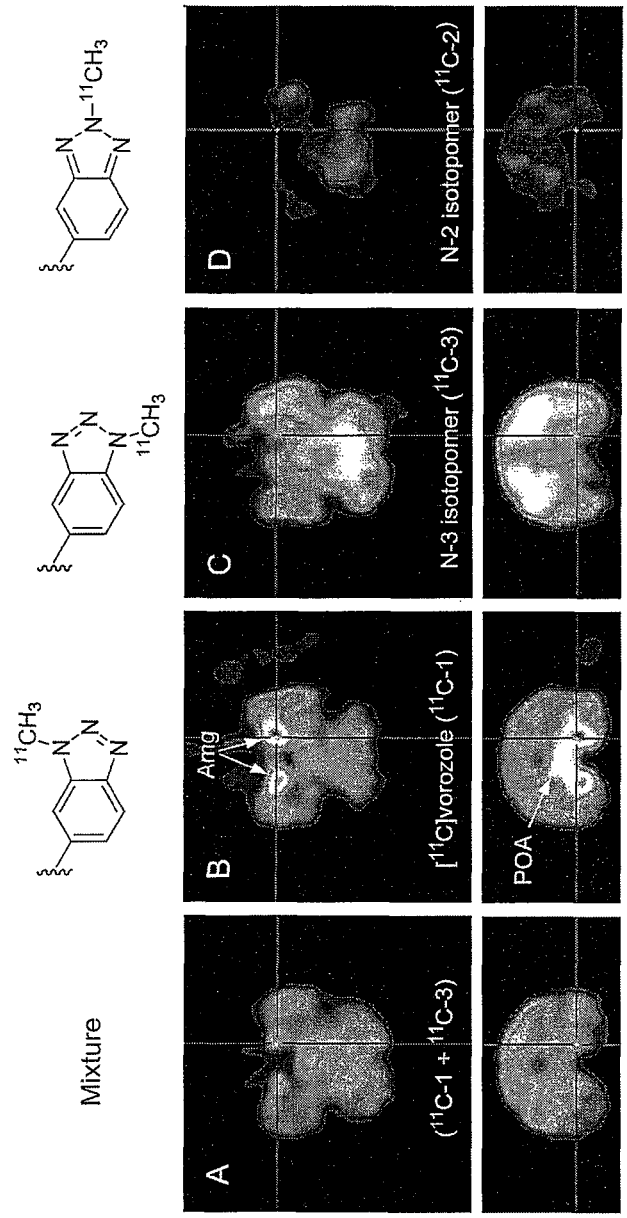
FIG. 3: PET images in the (transaxial (top row) and coronal (bottom row) planes in baboon brain summed from 15-90 min after injection for (A) the 15 minute fraction (X), (mixture of structure 3 and structure 4, 176.49 MBq (4.77 mCi)), (B) [N-methyl-$^{11}$C]vorozole (structure 3, 163.91 MBq (4.43 mCi)); (C) N-3 isomer (structure 4, 123.21 MBq (3.33 mCi)) and (D) N-2 isomer (structure 5, 44.77 MBq (1.21 mCi)). All PET images are dose-corrected. Arrows indicate the amygdala (Amg) and preoptic area (POA).

FIG. 3 compares PET images of the 15 minute fraction (mixture of [N-methyl-$^{11}$C] vorozole and the labeled N-3 isomer), [N-methyl-$^{11}$C] vorozole, labeled N-3 isomer and labeled N-2 isomer at the levels of the amygdala (top row) and preoptic area (POA) (bottom row). These images showed (1) low signal to background of the aromatase-rich amygdala and no specific uptake in the POA for the mixture; (2) high retention in amygdala and preoptic area for [N-methyl-$^{11}$C]vorozole and (3) no specific uptake in amygdala and preoptic area for either of the isolated N-3 or N-2 isomers. Low signal to background for the mixture is consistent with contamination of the N-1 isomer whereas the high signal to noise in the amygdala and preoptic areas for pure vorozole (N-1 isomer) was consistent with the high affinity of vorozole for aromatase. We note that affinity values for the two non-vorozole isomers for aromatase are not available though we would predict low affinities relative to vorozole ($IC_{50}$=2.7 nM)[29] based on our imaging results (see Wouters, et al. (1989) J. Steroid. Biochem. Mol. Biol. 34:427-430).

Time-activity curves for pure [N-methyl-$^{11}$C]vorozole in the baboon brain revealed very high initial uptake in five brain regions (amygdala, cerebellum, frontal cortex, white matter and preoptic area). Carbon-11 peaked at ~5 min and cleared to a low point at 20-30 min and relatively stable accumulation through the end of the study in all brain regions. Regions with the highest accumulation of radiotracer were the amygdala and the preoptic area, both of which are rich in aromatase. Pretreatment with "cold" vorozole or letrozole reduced [N-methyl-$^{11}$C]vorozole accumulation in all brain regions examined, indicating its specificity to brain aromatase. After vorozole treatment there is a rapid but lower initial uptake followed by a steady clearance and no accumulation of [N-methyl-$^{11}$C]vorozole for both the amygdale and the preoptic brain regions. A similar pattern after pretreatment was seen for other brain regions.

Both of the other labeled isomers (N-3 and N-2) show reasonably high brain penetration (0.02-0.03% ID/cc at 2.5 min, data not shown) but no specific distribution to aromatase-rich brain regions.

Analysis of chemical form of C-11 in plasma after administration of [N-methyl-$^{11}$C]vorozole, labeled N-3 isomer and labeled N-2 isomer in the baboon: For all baboon studies, total C-11 in plasma was measured and the unchanged fraction of C-11 labeled compound was determined by HPLC. The % unchanged C-11 labeled vorozole in baboon plasma was high (up to 78-80% at 90 min).

Interestingly, the position of the methyl group seems to exert a considerable effect on the metabolism, in that N-2 and N-3 isomers showed very rapid appearance of labeled metabolites and inter-subject variability seemed high compared with labeled vorozole. However, the area under curves (AUCs) for labeled vorozole and the labeled N-3 isomer in plasma normalized to the injected dose over 90 minutes were similar, suggesting that the contribution of the N-3 isomer in the PET image of the mixture would be significant. The labeled N-2 isomer showed a rapid rate of disappearance of the parent labeled compound from plasma.

Recent use of $^{11}CH_3$ vorozole, substantially separated from the N-3 radio-methyl isomer, in PET imaging of brains of healthy male and female human volunteers showed a strikingly different distribution pattern than the pattern found in rodents and non-human primates. In humans the highest levels were found in distinct thalamic nuclei and moderately high levels were found in amygdale, preoptic area and the medulla.

The invention claimed is:

1. A method of preparing N-1 radio-methyl vorozole substantially separated from an N-3 radio-methyl isomer comprising:
   a) providing a mixture comprising radio-methyl vorozole and radio-methyl N-3 isomer;
   b) applying said mixture, under suitable conditions, to a chromatography resin offering multiple mechanisms for selectivity;
   c) eluting said compounds using an eluent comprising aqueous formic acid:methanol;
   thereby obtaining a composition consisting of N-1 radio-methyl vorozole.

2. The method according to claim 1 wherein the mixture optionally further comprises a radio-methyl N-2 isomer.

3. The method according to claim 1 wherein the multiple mechanisms of selectivity include at least two of hydrogen bonding, dipole-dipole interaction, aromatic Π-Π interaction and hydrophobic interaction.

4. The method according to claim 3 wherein the resin comprises aromatic components and alkyl components.

5. The method according to claim 4 wherein the resin optionally further comprises halogen components.

6. The method according to claim 5 wherein the halogen component is fluorine.

7. The method according to claim 6 wherein the resin is a pentafluorophenylpropyl (PFPP) resin.

8. The method according to claim 4 wherein the resin comprises a phenoxypropyl resin.

9. The method according to claim 1 wherein the eluent comprises aqueous formic acid:methanol in ratios varying between 1:1 and 1:2.

10. The method according to claim 9 wherein the ratio varies between 1:1 and 1:1.5.

11. The method according to claim 10 wherein the ratio varies between 1:1 and 1:1.2.

12. The method according to claim 1 wherein the aqueous formic acid is adjusted to a pH between about 2.0 and about 4.5.

13. The method according to claim 12 wherein the pH is between about 2.5 and about 3.5.

14. The method according to claim 1 wherein the N-1 radiomethyl vorozole and the N-3 radiomethyl vorozole isomer are [$^{11}$C]-radiomethyl radiomethyl vorozole and vorozole isomers, respectively.

15. The method according to claim 14 wherein the $^{11}$C-vorozole and vorozle isomer are formed through methylation of norvorozole with [$^{11}$C]Methyl iodide.

16. The method according to claim 2 wherein the N-1 radiomethyl vorozole and the N-2 and the N-3 radiomethyl vorozole isomers are [$^{11}$C]-methyl vorozole and [$^{11}$C]-methyl vorozole isomers, respectively.

17. The method according to claim 16 wherein the [$^{11}$C]-methyl vorozole and [$^{11}$C]-methyl vorozole isomers are formed through methylation of norvorozole with [$^{11}$C]Methyl iodide under conditions for complete methylation of norvorozole.

18. The [$^{11}$C]N1-methyl vorozole prepared by any one of the methods of claim 14-17.

19. A method of preparing N1-radio-methyl vorozole substantially separated from N2- and N3-radio-methyl isomers of vorozole comprising:

a) providing a mixture comprising N1-radio-methyl vorozole, N2-radio-methyl isomer and N3-radio-methyl isomer;
b) applying said mixture, under suitable conditions, to a chromatography resin selected from the group consisting of pentafluorophenylproply (PFPP) resin and phenoxypropyl resin; and
c) eluting said compounds using an eluent comprising aqueous formic acid:methanol;

thereby obtaining a composition consisting of N1-radio-methyl vorozole.

20. The method according to claim 19 wherein the mixture of N1-radio-methyl vorozole, N2-radio-methyl isomer and N3-radio-methyl isomer is provided through methylation of norvorozole with radio-Methyl iodide.

21. The N1-radio-methyl vorozole prepared by the method of claim 20.

* * * * *